United States Patent
Kornienko et al.

(10) Patent No.: US 10,781,226 B2
(45) Date of Patent: Sep. 22, 2020

(54) PHOTOACTIVATABLE CANCER PRODRUG

(71) Applicants: Texas State University, San Marcos, TX (US); LEIDEN UNIVERSITY, Leiden (NL)

(72) Inventors: Alexander Kornienko, San Marcos, TX (US); Tania Betan-Court, San Marcos, TX (US); Sylvestre Bonnet, Amsterdam (NL); Vincent Van Rixel, Amsterdam (NL)

(73) Assignees: Texas State University, San Marcos, TX (US); Leiden University, Leiden (NL)

( * ) Notice: Subject to any disclaimer, the term of this patent is extended or adjusted under 35 U.S.C. 154(b) by 0 days.

(21) Appl. No.: 16/757,370

(22) PCT Filed: Oct. 19, 2017

(86) PCT No.: PCT/US2017/057418
§ 371 (c)(1),
(2) Date: Apr. 17, 2020

(87) PCT Pub. No.: WO2019/078871
PCT Pub. Date: Apr. 25, 2019

(65) Prior Publication Data
US 2020/0239503 A1    Jul. 30, 2020

(51) Int. Cl.
*C07F 15/00* (2006.01)
(52) U.S. Cl.
CPC .................................... *C07F 15/00* (2013.01)
(58) Field of Classification Search
CPC ..................................................... C07F 15/00
See application file for complete search history.

(56) References Cited

U.S. PATENT DOCUMENTS

| | | |
|---|---|---|
| 8,946,246 B2 | 2/2015 | Magedov et al. |
| 9,290,528 B1 | 3/2016 | Glazer et al. |
| 9,334,280 B2 | 5/2016 | Magedov et al. |
| 2008/0221136 A1 | 9/2008 | Bogevig et al. |
| 2012/0220922 A1 | 8/2012 | Yuste et al. |
| 2013/0331367 A1 | 12/2013 | McFarland |
| 2014/0148425 A1 | 5/2014 | Bonnet |
| 2016/0101177 A1 | 4/2016 | Papish et al. |
| 2016/0206653 A1 | 7/2016 | Mandel |

FOREIGN PATENT DOCUMENTS

WO    2012/052821    4/2012

OTHER PUBLICATIONS

International Search Report and Written Opinion for PCT Application No. PCT/US2017/057418 dated Jan. 8, 2018.
Askes et al. "Activation of a Photodissociative Ruthenium Complex by Triplet-Triplet Annihilation Upconversion in Liposomes" Angewandte Chemie International Edition (2014) 53:4, pp. 1029-1033.
Bonnet et al. "Ruthenium-Decorated Lipid Vesicles: Light-Induced Release of [Ru(terpy)(bpy)(OH2)]2+ and Thermal Back Coordination" J. Am. Chem. Soc. 2011, 133, 252-261.
Goldbach et al. "N-Acetylmethionine and Biotin as Photocleavable Protective Groups for Ruthenium Polypyridyl Complexes" Chemistry—A European Journal (2011) 17(36), 9924-9929.
Huisman et al "Caging the uncageable: using metal complex release for photochemical control over irreversible Inhibition" J. Chem. Commun. (2016) 52, 12590.
Lopez "On the Development of Dually-Responsive PNIPAM Copolymers" Master Thesis submitted at the University of Strasbourg & University of Freiburg, Sep. 2016.
Mackay et al. "A Potent cytotoxic photoactivated platinum complex" PNAS (2007), 104, 20743-20748.
Medellin et al. "Novel Microtubule-Targeting 7-Deazahypoxanthines Derived from Marine Alkaloid Rigidins with Potent in Vitro and in Vivo Anticancer Activities" J Med Chem. (2016) 59(1), 480-485.
Niedre et al. "Direct Near-Infrared Luminescence Detection of Singlet Oxygen Generated by Photodynamic Therapy in Cells In Vitro and Tissues In Vivo" Photochemistry and Photobiology (2002) 75(4) 382-391.
Novakova et al. "Correlation between Cytotoxicity and DNA Binding of Polypyridyl Ruthenium Complexes" Biochemistry (1995) 34 12369.
Pyle et al "Mixed-Ligands Complexes of Ruthenium(II): Factors Governing Binding to DNA" J. Am. Chem. Soc. (1989) 111, 3051-3058.
Snyder et al. "Photodynamic Therapy: A Means to Enhanced Drug Delivery to Tumors" Cancer Research (2003) 63,8126-8131.
Yang et al. "Tuning of Redox Potentials by Introducing a Cyclometalated Bond to Bis-tridentate Ruthenium(II) Complexes Bearing Bis(N-methylbenzimidazolyl)benzene or -pyridine Ligands" Inorg. Chem. (2012) 51, 890-899.
Zayat et al. "A New Strategy for Neurochemical Photodelivery: Metal-Ligand Heterolytic Cleavage" J. Am. Chem. Soc. (2003) 125, 882-883.

*Primary Examiner* — Paul V Ward
(74) *Attorney, Agent, or Firm* — Kowert, Hood, Munyon, Rankin & Goetzel, P.C.; Mark R. DeLuca (57) ABSTRACT

Described herein is photocaging methodology using ruthenium (II) complexes with 7-deazahypoxanthine-based anticancer agents. Specifically, 7-deazahypoxanthines are converted into photoactivatable chemotherapeutic agents for the controlled release of these toxic agents selectively into tumor tissue upon irradiation with light.

7 Claims, 3 Drawing Sheets

PHOTOACTIVATABLE CANCER PRODRUG

BACKGROUND OF THE INVENTION

1. Field of the Invention

The invention generally relates to photoactivatable compounds. More specifically, the present invention relates to photoactivatable ruthenium compounds and use of such compounds for the treatment of cancer.

2. Description of the Relevant Art

Microtubules are important components of the cytoskeleton and play several crucial roles in a diverse array of cellular processes such as morphogenesis, motility, organelle and vesicle trafficking, and chromosome segregation during mitosis. Furthermore, alteration of tubulin polymerization disrupts the formation of tumor vasculature, and it is not surprising that the microtubule cytoskeleton has emerged as an effective target for cancer chemotherapy. Microtubule-targeting agents, such as vinca alkaloids and taxanes, have been used in clinic over 50 years. In past decades, new antimicrotubule agents that possess different structure and binding sites of tubulin have shown potent activity against the proliferation of various cancer cells, as well as in multidrug-resistant cancers. Interestingly, many of these agents represent an attractive ability that targeting the tumor blood vessels results in tumor vascular disruption. Therefore, exploring new agents and strategies may provide more effective therapeutic options in the related treatment of cancer.

A major problem of treatment with anticancer chemotherapy drugs, including those that target microtubules, is that such treatment is often toxic to noncancerous cells, creating systemic side effects. Various strategies, including tumor-targeted drug delivery, target site-activated prodrugs, and combination therapy, have been proposed to minimize such systemic side effects. These strategies have a shared goal of keeping the systemic concentration of the drug lower than its toxic level while the drug concentration at tumor sites is kept above the effective concentration.

With that goal, photodynamic therapy (PDT) provides an excellent foundation for inspiring a new strategy for treating tumors. In PDT, nontoxic photosensitizers are activated by tissue-penetrable light (630-800 nm in the red and NIR range) to locally generate short-lived reactive oxygen species (ROS) such as singlet oxygen (SO) to ablate cancer cells while causing only minimal side effects.

PDT is attractive because it is minimally invasive, spatially accurate and can treat organs where surgery is highly debilitating. It is particularly suited for skin, lung or gastrointestinal cancers, for which the source of light can be easily directed on the tumors. It is also possible to shine light on internal organs using endoscopy to treat prostate, head and neck, brain, bile duct or bladder cancers for example; this is called "interstitial PDT". Several photosensitizers for PDT have been clinically approved so that light irradiation techniques are now available in hospitals.

However, many types of cancer, including recurrent superficial bladder cancer, non-resectable cholagiocarcinomas, head and neck cancer, brain cancer, or esophageal cancer, respond poorly to PDT. An important reason for such recalcitrance is poor oxygenation of tumor tissues. One solution to the poor oxygenation of tumor tissues is the use of a photosensitive prodrug that upon photocleavage does not require oxygen (unlike PDT) to generate the active drug. Such prodrugs, which are rendered inactive through covalent modification with a photocleavable moiety but can regain biological activity upon light exposure, are commonly referred to as "photocaged" compounds. Light-activatable pro-moieties allow the modulation of the release and activity of a "photocaged" drug as a function of the wavelength, duration, intensity, or location of illumination.

BRIEF DESCRIPTION OF THE DRAWINGS

Advantages of the present invention will become apparent to those skilled in the art with the benefit of the following detailed description of embodiments and upon reference to the accompanying drawings in which.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Unless defined otherwise, all technical and scientific terms used herein have the same meaning as commonly understood by one of ordinary skill in the art.

The term "alkyl" as used herein generally refers to a radical substituent containing the monovalent group $C_nH_{2n+1}$, where n is an integer greater than zero. In some embodiments n is 1 to 12. The term "alkyl" includes a branched or unbranched monovalent hydrocarbon radical. Examples of alkyl radicals include, but are not limited to: methyl, ethyl, propyl, isopropyl, butyl, iso-butyl, sec-butyl, pentyl, 3-pentyl, hexyl, heptyl, octyl, nonyl, decyl, undecyl, dodecyl. When the alkyl group has from 1-6 carbon atoms, it is referred to as a "lower alkyl" or a "$C_1$-$C_6$ alkyl."

Suitable lower alkyl radicals include, but are not limited to, methyl, ethyl, n-propyl, i-propyl, 2-propenyl (or allyl), n-butyl, t-butyl, and i-butyl (or 2-methylpropyl).

The term "carbocyclic" as used herein generally refers to a ring structure in which all the atoms composing the ring are carbon atoms. A "saturated carbocyclic" is a ring-shaped molecule, wherein the ring portion of the molecule has the general formula $C_nH_{2n-1}$, where n is an integer of 3 or greater, and wherein the carbons $C_1$ and $C_n$ are coupled to each other to form a ring. In some embodiments n is 3 to 8. Examples of saturated carbocycles include, but are not limited to: cyclopropyl (n=3), cyclobutyl (n=4), cyclopentyl (n=5), cyclohexyl (n=6), cycloheptyl (n=7), and cyclooctyl (n=8). An "unsaturated carbocyclic" is a carbocyclic ring having one or more double-bonds or triple bonds between carbon atoms forming the ring portion of the molecule.

The term "haloalkyl" as used herein generally refers to alkyl radicals that include one or more halogen atoms attached to any carbon of the alkyl radical in place of a hydrogen atom.

As used herein the terms "alkenyl" and "olefin" generally refer to any structure or moiety having the unsaturation C=C. Examples of alkenyl radicals include, but are not limited to vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl.

As used herein, the term "alkynyl" generally refers to any structure or moiety having the unsaturation C≡C. Examples of alkynyl radicals include, but are not limited to: ethynyl, 1-propynyl, 2-propynyl, 1-butynyl, 2-butynyl, and 3-butynyl.

The term "aryl" is used to refer to a benzene ring that includes one or more substituents. The term "fused aryl" is used to refer to multiple benzene rings which are fused together and where one or more of the fused benzene rings includes one or more substituents. Fused aryl groups include, but are not limited to substituted naphthalene, anthracene, phenanthrene, chrysene, and pyrene. Substituents attached to the aryl or fused aryl group include, but are not limited to, alkyl groups, halogen atoms, nitro groups, carboxyl groups, benzyl, alkoxy, hydroxy, and phenoxy. Substituents may be attached at any position on the aryl radical which would otherwise be occupied by a hydrogen atom.

The term "arylalkyl" is used to refer to an "aryl" group as defined above, which includes at least one alkyl substituent. Commonly, the alkyl substituent is a lower alkyl substituent.

The term "arylalkenyl" is used to refer to an "aryl" group as defined above, which includes at least one alkene substituent.

The term "arylalkynyl" is used to refer to an "aryl" group as defined above, which includes at least one alkyne substituent.

The term "alkylacyl" denotes groups —C(O)R where R is alkyl as defined herein.

The term "cycloalkylacyl" denotes groups —C(O)R where R is a cycloalkyl. Examples of cycloalkylacyl compounds include, but are not limited to, cyclopropylacyl-, cyclopentylacyl and cyclohexylacyl.

The term "alkoxy" generally refers to an —OR group, where R is a lower alkyl, substituted lower alkyl, aryl, substituted aryl, aralkyl or substituted aralkyl. Suitable alkoxy radicals include, but are not limited to, methoxy, ethoxy, phenoxy, t-butoxy, methoxyethoxy, and methoxymethoxy.

The term "heterocycle" as used herein generally refers to a closed-ring structure, in which one or more of the atoms in the ring is an element other than carbon. Heterocycle may include aromatic compounds or non-aromatic compounds. Aromatic heterocyclic compounds are also referred to as "heteroaryls." Heteroaryls may include rings such as thiophene, pyridine, isoxazole, phthalimide, pyrazole, indole, furan, or benzo-fused analogs of these rings. Examples of non-aromatic heterocycles include tetrahydrofuran, morpholine, piperidine, pyrrolidine, and others. In some embodiments, a "heterocycle" is a stable 5- to 7-membered monocyclic or bicyclic or 7- to 10-membered bicyclic heterocyclic ring which is either saturated or unsaturated, and which consists of carbon atoms and from 1 to 4 heteroatoms (e.g., N, O, and S) and wherein the nitrogen and sulfur heteroatoms may optionally be oxidized, and the nitrogen may optionally be quaternized, and including any bicyclic group in which any of the above-defined heterocyclic rings is fused to a benzene ring. In some embodiments, heterocycles may include cyclic rings including boron atoms. The heterocyclic ring may be attached to its pendant group at any heteroatom or carbon atom that results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

The term "heteroarylalkyl" is used to refer to a "heteroaryl" group as defined above, which includes at least one alkyl substituent. Commonly, the alkyl substituent is a lower alkyl substituent.

The term "heteroarylalkenyl" is used to refer to a "heteroaryl" group as defined above, which includes at least one alkenyl substituent.

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

In an embodiment, a photosensitive compound has the structure (I):

(I)

where:
each $R_1$ and $R_2$ is selected from hydrogen, phenyl, aryl, fused aryl, heteroaryl, saturated carbocyclic, unsaturated carbocyclic, non-aromatic heterocycle, aromatic heterocycle saturated heterocyclic groups, $C_1$-$C_6$ alkyl, haloalkyl, alkenyl, alkynyl, arylalkyl, arylalkenyl, arylalkynyl, heteroarylalkyl, heteroarylalkenyl, cycloalkylacyl, heteroarylalkyl, alkoxy, aminoalkyl, carboxyalkyl, nitroalkyl, cyanoalkyl, acetamidoalkyl, and acyloxyalkyl, wherein in each alkyl, aryl, cycloalkyl or heteroaryl one or more available hydrogens can optionally be replaced by fluorine;
$R_3$ is alkyl or aryl;
$R_4$ is alkyl, acyl, aryl, alkoxycarbonyl, or sulfonyl; and
n is 1-6.

The Ru(II) Complex forms a photocleavable bond with the sulfur atom of the $R_3S$ group. In some embodiments, the sulfur-ruthenium bond is cleaved upon irradiation with light having a wavelength between about 400 nm to about 1400 nm, thereby generating a pharmacologically active 7-deazahypoxanthine. Use of a thioether as a ligand for ruthenium offers a number of advantages over the use of nitrogen-based ligands. First, like primary amines and pyridines but unlike thiols, thioethers are excellent ligands for Ru(II) because they are softer than nitrogen. Second, thioethers are less prone to protonation in acidic medium than amines for example. Third, thioethers are photoreleased with much higher quantum yields than pyridine or amines, in particular with sterically unhindered ruthenium-based photocaging groups. Finally, thioethers are much more difficult to oxidize than thiols. Overall, when coordinated to Ru complexes, thioethers produce stable coordination bonds in the dark, but bonds that can be broken when irradiated with light at the appropriate wavelength.

The Ru(II) Complex, in some embodiments, has the structure (II):

(II)

The group represents a tridentate ligand coupled to ruthenium via three nitrogen-ruthenium bonds.

The group represents a bidentate ligand coupled to ruthenium via two nitrogen-ruthenium bonds.

The tridentate ligand has three nitrogen groups that can be bonded to the ruthenium. Exemplary tridentate ligands include, but are not limited to:

where each $R_5$, independently, is: hydroxy, H, $C_1$-$C_4$ alkyl, carboxy, alkoxy, amino, N,N-dimethylamino, carbonyl, halide, alkyne (C≡CH), sulfonato, or nitro group. Each $R_6$ is H, Me, Et, Pr, Bu, or halide.

The bidentate ligand has two nitrogen groups that can be bonded to the ruthenium. Exemplary bidentate ligands include, but are not limited to:

where each $R_5$, independently, is: hydroxy, H, $C_1$-$C_4$ alkyl, carboxy, alkoxy, amino, N,N-dimethylamino, carbonyl, halide, sulfonato, or nitro group.

In an embodiment, the photosensitive compound has the structure:

(III)

Where each $R_1$ and $R_2$ is selected from hydrogen, phenyl, aryl, $C_1$-$C_6$ alkyl, haloalkyl, hydroxyalkyl, aminoalkyl, carboxyalkyl, nitroalkyl, cyanoalkyl, acetamidoalkyl, and acyloxyalkyl, and where $R_4$ is alkyl, acyl, aryl, alkoxycarbonyl, or sulfonyl.

In an embodiment, photosensitive compound has the structure (IV):

(IV)

In order to render the photosensitive compounds described herein active for the treatment of cancer, the compounds of the present invention are subjected to light, so as to convert the compounds from substantially inactive compounds to compounds that are highly active toward cancer cells.

A feature of the present invention is that the light activation desirably takes place in the body, or within cells, and that the photoreleased molecule exhibits activity against cancer cells.

Light of any suitable wavelength may be used to cause activation of the complexes of the present invention. However, desirably the light may be in the visible ranges, i.e. with a wavelength between 400 and 800 nm. Alternatively, near infrared radiation might be used that penetrate better into biological tissues.

The complexes of the present invention are typically positively charged. In that case, a counterion is necessary to balance the charge of the complex and provide a molecular species with an overall charge of zero. Negatively charged counter ions may be any suitable ion, for example selected from $BF_4$, $BPh_4$, $PF_6$, triflate, mesylate, tosylate, trisphat, halides (such as chlorides), nitrate, sulfate, carbonate and phosphate. The counter ion may be chosen for certain purposes, for example, to provide a useful advantage for the compound preparation or better suitability for pharmaceutical/medical uses. In some embodiments, the complex may be neutral or have a negative charge (with a positive counterion) if negatively charged ligands are used. For example, placing a sulfonate group ($—SO_3^-$) as a substituent on an nitrogen heteroaryl ring (for example tridentante or bidentate ligands substituted with sulfonate as $R_5$ will create a negatively charged ligand.

Any suitable route of administration may be employed for providing a patient with an effective dosage of the photosensitive compounds described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In certain embodiments, it may be advantageous that the compositions described herein be administered orally. The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.
7-Deazahypoxanthine—Ru(II) Complex In an example, a thioether-containing 7-deazahypoxanthine 1 is converted into photoactivatable chemotherapy complex $[2](PF_6)_2$ for the controlled release of the 7-deazahypoxanthine selectively into tumor tissue upon irradiation with light. As is illustrated with the data provided below, complex $[2](PF_6)_2$ is an excellent photoactivatable prodrug of 1 because it is only weakly active against cancer cells in vitro. However, photorelease of 1 from $[2](PF_6)_2$ using blue or green light results in dramatic increase of cytotoxicity and could be the basis for a highly selective photoactivated chemotherapy. Furthermore, the cytotoxicity of the ruthenium aqua complex also released by light irradiation, ie $[Ru(terpy)(bpy)(OH_2)]^{2+}$, is very low, so that for these caged compounds phototoxicity is mostly caused by the uncaged 7-deazahypoxanthine inhibitor 1.

1

$[2](PF_6)_2$

Synthesis

Thioether-containing 7-deazahypoxanthine 1 was prepared using the procedure published by Medellin et al. "Novel Microtubule-Targeting 7-Deazahypoxanthines Derived from Marine Alkaloid Rigidins with Potent in Vitro and in Vivo Anticancer Activities" *J. Med. Chem.* 2016, 59, 480-485, which is incorporated herein by reference.

Complex [Ru(tpy)(bpy)(1)](PF$_6$)$_2$ ([2](PF$_6$)$_2$) was synthesized by reacting 1 with 2 equivalents of [Ru(tpy)(bpy)(OH$_2$)](PF$_6$)$_2$ ([3](PF$_6$)$_2$) as shown in Scheme 1. Reaction was performed by reacting 0.5 eq. of 1 with [3](PF$_6$)$_2$ at 100° C. in ethylene glycol under nitrogen for 16 hours affording product [2](PF$_6$)$_2$ in 20% yield.

Scheme 1

In a 2-necked round-bottom flask compound [3](PF$_6$)$_2$ (75 mg, 0.48 mmol) and compound 1 (22 mg, 0.25 mmol) were added in ethylene glycol (10 mL) under argon. The solution was stirred overnight at 100° C. under argon resulting in a red solution. The reaction mixture was added to a dichloromethane (DCM) and KPF$_6$-saturated water mixture. After full extraction to the DCM layer, the DCM was washed with KPF$_6$-saturated water to remove ethylene glycol. After evaporation in vacuo, the crude was dissolved in acetone and purified by size exclusion chromatography (Sephadex, LH-20 in acetone). After evaporation in vacuo the product was reprecipitated from acetone by the addition of diethyl ether and obtained as a red powder. Yield: 13 mg.

Column-Free Synthesis [2](PF$_6$)$_2$

[Ru(tbpy)(bpy)(OH$_2$)](PF$_6$)$_2$ (0.198 g, 0.248 mmol) and 1 (0.050 g, 0.124 mmol) were weighed in a 2-neck 25 mL flask. The flask was put into a reflux-condenser heating set-up and the system was purged with N$_2$. Ethylene glycol (5 mL) was added and the reaction mixture suspension was stirred overnight at 100° C. under nitrogen atmosphere. After TLC was performed to ensure full conversion of rigidin (eluent: Acetone/water/KPF$_{6,sat}$ 16:4:1) the reaction was cooled to room temperature. Then, saturated aqueous KPF$_6$ was added (10 mL), upon which precipitation occurred. Upon filtration a red powder was obtained that was washed with demineralized water (3×10 mL) and diethyl ether (3×10 mL). The powder was then dissolved in acetone (2×10 mL), collected in a round-bottom flask, and saturated aqueous KPF$_6$ solution (20 mL) was added. Then, the flask was attached to a rotary-evaporation set-up (200-100 mbar, 40° C.) and the acetone was evaporated upon which precipitation of the target complex occurred. The precipitate was collected on a filter and washed with water (3×10 mL) and diethyl ether (3×10 mL). The powder was dried in vacuo. Yield: 75%.

1H NMR (500 MHz, CD3OD): δ=9.74 (d, J=5.5 Hz, 1H, A6), 8.82 (d, J=8.0 Hz, 1H, A3), 8.72 (d, J=8.0 Hz, 2H, D3+D3'), 8.69 (d, J=8.0 Hz, 1H, B3), 8.51 (t, J=8.0 Hz, 2H, C3+C3'), 8.39 (dd, J=8.0, 1.2 Hz, 1H, A4), 8.37 (dd, J=8.4, 1H, D4), 8.03 (ddd, J=7.8 Hz, 5.5 Hz, 1.5 Hz, 1H, A5), 7.95 (dd, J=8.0 Hz, 2H, C4+C4'), 7.92 (dd, J=7.5 Hz, 1.5 Hz), 1H, B4), 7.73 (d, J=5.5 Hz, 2H, C6), 7.52 (dd, J=8.5, 1.0 Hz, 2H, Ph), 7.35 (ddd, J=0.5, 6.0, 6.0 Hz, 2H, C5), 7.32-7.18 (m, 5H, Ph+B5), 7.14-7.05 (m, 5H, Ph+B6), 2.63 (t, J=6 Hz, 2H, CH2), 1.91 (p, J=7.0 Hz, 2H, CH2), 1.91 (t, J=7.5 Hz, 2H, CH2), 1.47 (s, 3H, CH3). 13C NMR (125 MHz, CD3OD): δ=190.4 (C=O), 161.7 (pp), 159.2 (pp), 158.8 (pp), 158.7 (pp), 158.1 (pp), 158.1 (pp), 154.2 (Ph), 153.0 (Ph), 151.2 (Ph), 150.8 (Ph), 140.1 (Ph), 139.6 (C4), 138.6 (py-q), 138.3 (D4), 133.7 (py-q), 133.3 (A6), 132.6 (Ar), 130.6 (Ar), 129.7 (Ar-q), 129.4 (Ar-q), 129.2 (A5), 129.1 (C5), 128.9 (Ar), 126.1 (C3'), 126.0 (C3), 125.4 (A3), 125.2 (D3), 32.8 (CH$_{2-r}$), 32.80 (CH$_{2-t}$), 23.7 (CH$_2$-pentet), 14.6 (CH$_3$).

Elem. Anal. Calcd. For C$_{48}$H$_{40}$F$_{12}$N$_8$O$_2$P$_2$RuS: C, 48.69; H, 3.41; N, 9.46. Found: C, 49.35; H, 3.53; N, 9.32

Photochemistry

Figure 1:
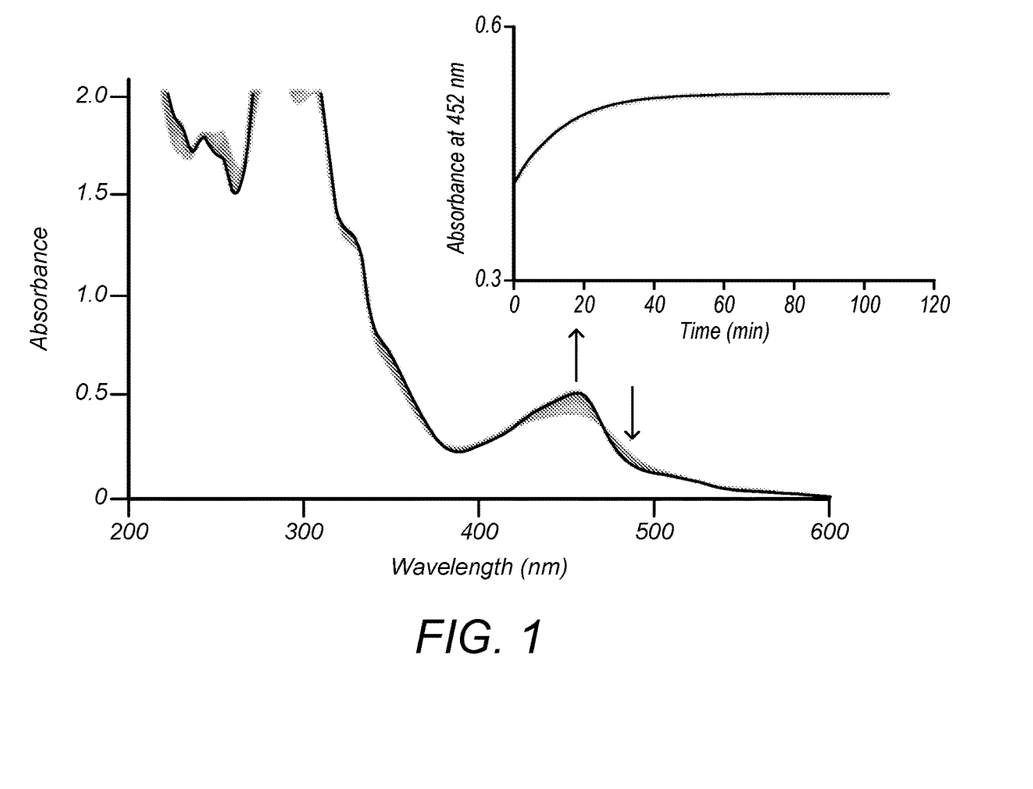
FIG. 1 depicts the evolution of the electronic absorption spectra of a solution of [2]($PF_6$)$_2$ in acetonitrile upon green light irradiation under nitrogen.

FIG. 1 depicts the evolution of the electronic absorption spectra of a solution of [2](PF$_6$)$_2$ in acetonitrile upon green light irradiation under nitrogen (λ=530 nm, Δλ1/2=25 nm, 6.02 mW, 4.1×10$^{-8}$ Einstein per s). Time: 0 min (red curve) to 30 min (yellow curve) Conditions [Ru]0=50 μM, irradiated volume was 3.0 mL at 293 K. Under green light irradiation ($\lambda_{irr}$=530 nm) and a nitrogen atmosphere a solution of [2](PF$_6$)$_2$ in acetonitrile resulted in a major increase of absorbance at 452 nm and a slight shift of the maximum from 452 nm 454 nm of the metal to ligand charge transfer ("MLCT") band as shown in FIG. 1. The absorbance at 452 nm in the inset in FIG. 1 shows that after 60 minutes no reaction is occurring. Mass spectrometry after light irradiation showed peaks at m/z=266.4 corresponding to [Ru(tpy)(bpy)(CH$_3$CN)]$^{2+}$ (calc. m/z=266.1), whereas the dark control shows a major signals at m/z=447.0 corresponding to [2](PF$_6$)$_2$$^{2+}$ (calc. m/z=447.1). Thus, ligand 1 was substituted by the solvent molecule acetonitrile. Similar evolutions were observed under blue light irradiation (450 nm), which allowed for measuring a photosubstitution quantum yield (ΦPS=0.6%). $^1$H NMR irradiation studies following the characteristic A6 proton at 9.66 ppm from the bpy ligand showed that after 5 minutes irradiation by white light and is fully replaced by a peak at 9.59 ppm indicating full conversion of the photosubstitution reaction. When the same irradiation reaction was performed in demineralized water followed by UV-vis spectroscopy, but Rayleigh scattering occurred upon precipitation of free 1, which has a maximum solubility of 10 μM in demineralized water. Thus, the Ru—S bond of [2]$^{2+}$ is photoactivatable in $CH_3CN$ with blue, green and white light and under our conditions full conversion was obtained.

Photocytotoxicity Studies

Table 1 shows Photocytotoxicity (EC50 with 95% confidence interval in µM) of [2](PF$_6$)$_2$, 1, [3](PF$_6$)$_2$ and cisplatin on skin (A375, A431) and lung (A549) cancer cell lines given with photo index (PI). In addition, the complexes were tested against a non-cancerous lung cell line (MRC-5) for comparison. [Ru(tpy)(bpy)(OH$_2$)](PF$_6$)$_2$ ([3](PF$_6$)$_2$) was included in the assay to ensure that cytotoxicity did not originate from the metal cage, while cisplatin (CDDP) was included as positive control. The effective concentrations (EC50), defined as the compound concentration that reduces cell viability by 50% compared to untreated wells, were measured in the dark and after light activation. Green light was chosen for the photocytotoxicity assay, since in vitro and in vivo it is much less toxic than blue or UV-light.

In the dark EC50 values of 1 fell between 0.160 µM and 0.233 µM for A375, A431, and MRC-5 cells, and at 6.51 µM for A549 cells. For [2](PF$_6$)$_2$ in the dark EC50 values of 7-14 µM in A375, A431, and MRC-5 cells were observed. For A549 cells an EC50 value of 35 µM was measured. [3](PF$_6$)$_2$ showed no activity across all tested cell lines, while CDDP had EC50 values between 0.85-3.06 µM. Thus, coordinating 1 to [Ru(tpy)(bpy)]$^{2+}$ strongly inhibits the cytotoxicity of 1 in the dark.

TABLE 1

| Cell Line | Light dose (J cm$^{-2}$) | 1 EC$_{50}$ (µM) | ±CI | (2)(PF$_6$)$_2$ EC$_{50}$ (µM) | ±CI | PI | (3)(PF$_6$)$_2$ EC$_{50}$ (µM) | CDDP EC$_{50}$ (µM) | ±CI |
|---|---|---|---|---|---|---|---|---|---|
| A375 | 0 | 0.160 | [0.079-0.053] | 6.77 | [1.73-1.38] | 21 | >100 | 0.85 | [0.09-0.08] |
| | 38 | 0.198 | [0.106-0.069] | 0.325 | [0.16-0.11] | | >100 | 0.87 | [0.07-0.06] |
| A431 | 0 | 0.233 | [0.032-0.028] | 13.77 | [3.87-3.92] | 28 | >100 | 2.81 | [0.31-0.28] |
| | 38 | 0.237 | [0.045-0.038] | 0.489 | [0.07-0.06] | | >100 | 3.06 | [0.43-0.37] |
| A549 | 0 | 6.51 | [2.032-1.55] | 35.42 | [11.5-8.71] | 4 | >100 | 1.26 | [0.62-0.41] |
| | 38 | 3.40 | [0.54-0.47] | 9.15 | [7.12-7.90] | | >100 | 1.97 | [0.36-0.30] |
| MRC-5 | 0 | 0.165 | [0.13-0.07] | 8.13 | [1.74-1.43] | 9 | >100 | 1.49 | [0.23-0.20] |
| | 38 | 0.34 | [0.27-0.15] | 0.67 | [0.49-0.28] | | >100 | 2.17 | [0.26-0.23] |

Although an identical dose of green light barely induces photocytotoxicity by itself, nor changes the cytotoxicity of 1, [3](PF$_6$)$_2$, or CDDP, a remarkable effect was measured for [2](PF$_6$)$_2$ when irradiated with green light (520 nm, 30 min, light dose 38 J cm$^{-2}$). EC50 values for A375, A431, A549, and MRC-5 cells were 0.325, 0.49, 9.15, and 0.67 µM increasing the cytotoxicity 21, 28, 4 and 12 times, respectively.

Figure 2:
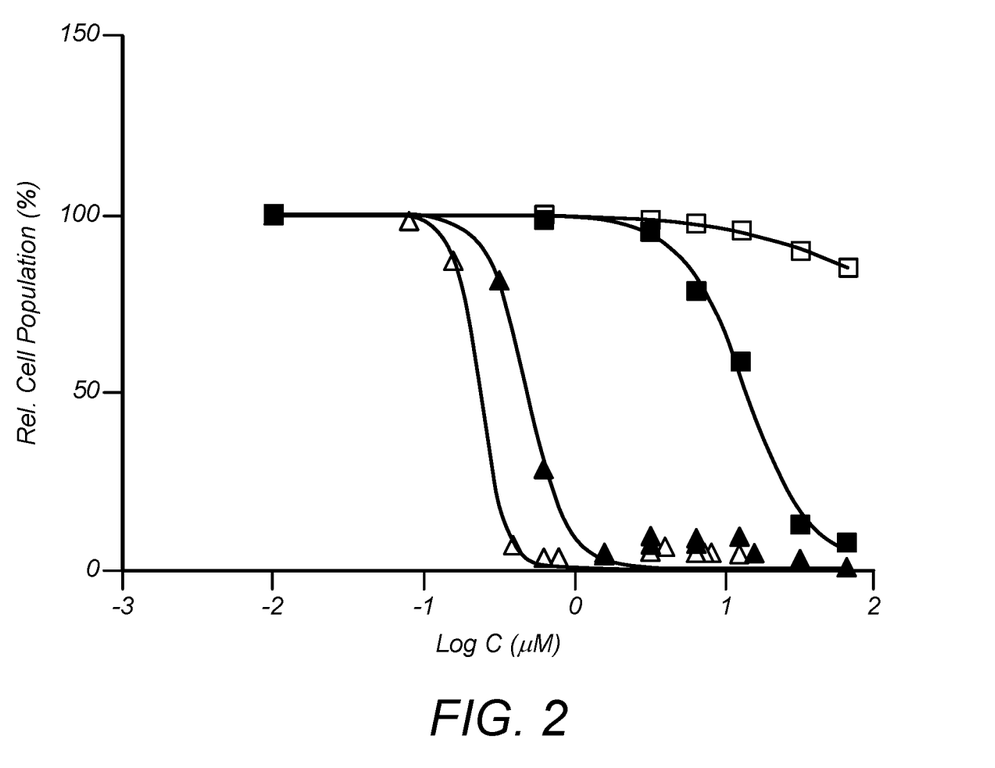
FIG. 2 depicts dose response curves for A431 cells incubated with 1 (light brown), [2]($PF_6$)$_2$ with irradiation (green), [2]($PF_6$)$_2$ without irradiation (black), and [3]($PF_6$)$_2$ (grey)

FIG. 2 depicts dose response curves for A431 cells incubated with 1 (light brown), [2](PF$_6$)$_2$ with irradiation (green), [2](PF$_6$)$_2$ without irradiation (black), and [3](PF$_6$)$_2$ (grey). Phototoxicity outline: cells seeded at $8\times10^3$ cells/well at t=0 h, treated at t=24 h, irradiated at t=30 h, and sulforhodamine B (SRB) assay performed at t=96 h. Incubation conditions: 37° C. and 7% CO$_2$. The curve of 1 is farthest left, indicating the highest cytotoxicity (EC50=0.233 µM), and its caged form in the dark—[2](PF$_6$)$_2$ —much more to the right, and therefore much less toxic (EC50=13.77 µM). However, uncaging 1 by green light irradiation of [2](PF$_6$)$_2$ shifts the dose response curve close to the dose response curve of 1 (EC50=0.49 µM). The dose response curve of [3](PF$_6$)$_2$ shows no reduction of cell viability by 50% at the highest concentration (100 µM) which is in line with existing literature. In short, [Ru(tpy)(bpy)]$^{2+}$ is an excellent cage for 1 because it strongly inhibits the activity when coordinated. Photosubstitution using green light releases 1, dramatically increasing the cytotoxicity of [2](PF$_6$)$_2$ and could be the basis for a highly selective photo activated chemotherapy.

Tubulin Polymerization

Figure 3:
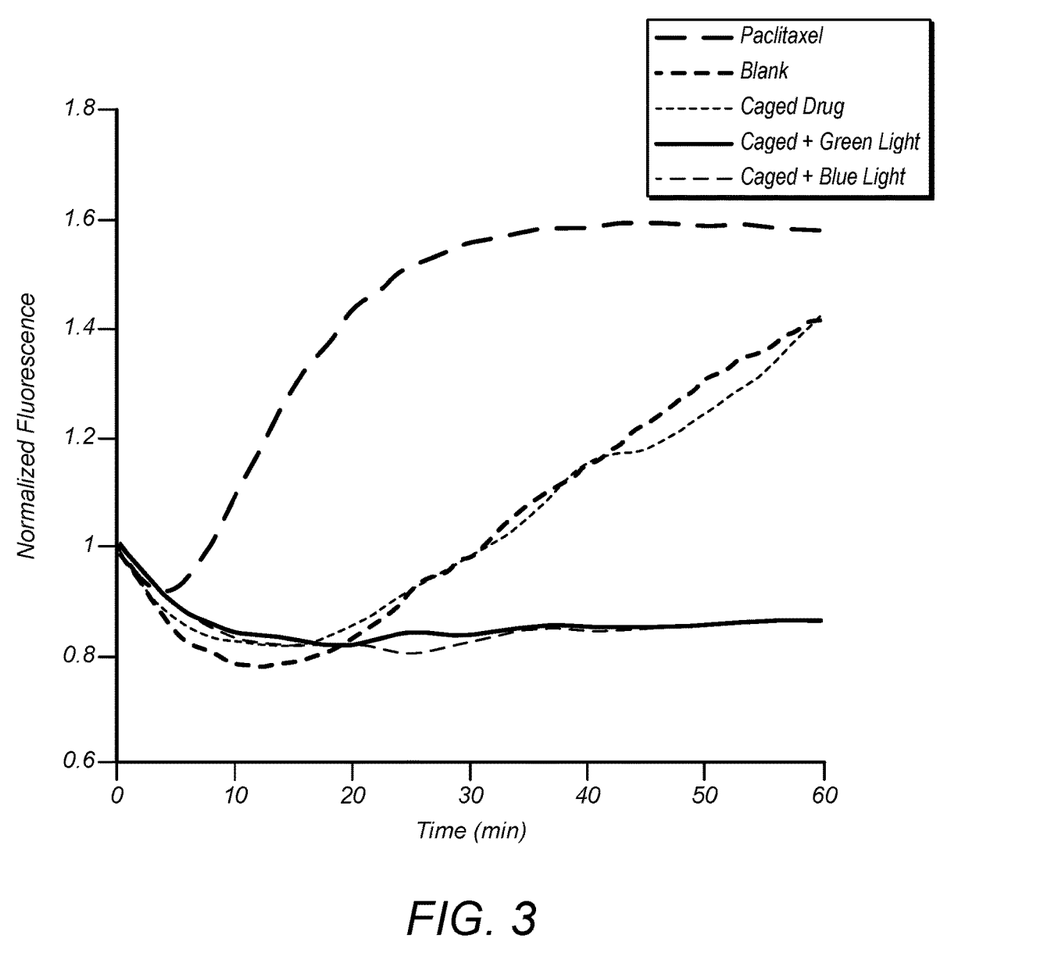
FIG. 3 shows the results of the tubulin polymerization assay. Raw fluorescence was normalized by initial fluorescence for each sample. Samples consists of the caged drug (not irradiated), the caged drug irradiated with green light, and the caged drug irradiated with blue light. Paclitaxel was utilized as a tubulin polymerization enhancer control.

To confirm that the mode of action of 1 does not change with the photocaging methodology, tubulin polymerization assay was conducted. FIG. 3 shows the fluorescence results of the tubulin polymerization assay. In this assay, increased fluorescence indicates tubulin polymerization. As expected, paclitaxel induces rapid polymerization of tubulin to form microtubules, leading to rapid increase in solution fluorescence. At a concentration of 25 µM, tubulin polymerization was completely inhibited with the caged drug that had been irradiated with either blue or green light, whereas no inhibition was observed with the caged drug without irradiation. This observation suggests that exposure to blue or green light is liberating the active agent and thereby enabling its inhibitory effect on tubulin polymerization.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A compound having the structure (I):

(I)

where:
each $R_1$ and $R_2$ is selected from hydrogen, phenyl, aryl, fused aryl, heteroaryl, saturated carbocyclic, unsaturated carbocyclic, non-aromatic heterocycle, aromatic heterocycle saturated heterocyclic groups, $C_1$-$C_6$ alkyl, haloalkyl, alkenyl, alkynyl, arylalkyl, arylalkenyl, arylalkynyl, heteroarylalkyl, heteroarylalkenyl, cycloalkylacyl, heteroarylalkyl, alkoxy, aminoalkyl, carboxyalkyl, nitroalkyl, cyanoalkyl, acetamidoalkyl, and acyloxyalkyl, wherein in each alkyl, aryl, cycloalkyl or heteroaryl one or more available hydrogens can optionally be replaced by fluorine;
$R_3$ is alkyl or aryl;
$R_4$ is hydrogen, alkyl, acyl, aryl, alkoxycarbonyl, or sulfonyl; and
n is 1-6;
wherein Ru(II) Complex forms a photoreleasable bond with the sulfur atom of the $R_3$—S group, wherein the sulfur-ruthenium bond is cleaved upon irradiation with light having a wavelength between about 400 nm to about 1400 nm.

2. The compound of claim 1, wherein the Ru(II) Complex has the structure:

(II)

wherein the group represents a tridentate ligand coupled to ruthenium via three nitrogen-ruthenium bonds; and
wherein the group represents a bidentate ligand coupled to ruthenium via two nitrogen-ruthenium bonds;
wherein structure (I) is:

3. The compound of claim 2, wherein the tridentate ligand is selected from the group consisting of:

, and where each $R_6$, independently, is: hydroxy, H, $C_1$-$C_4$ alkyl, carboxy, alkoxy, amino, N,N-dimethylamino, carbonyl, halide, alkyne (CCH), sulfonato, or nitro group; and
each $R_6$ is H, Me, Et, Pr, Bu, or halide.

4. The compound of claim 2, wherein the bidentate ligand is selected from the group consisting of:

where each $R_5$, independently, is: hydroxy, H, $C_1$-$C_4$ alkyl, carboxy, alkoxy, amino, N,N-dimethylamino, carbonyl, halide, sulfonato, or nitro group.

5. The compound of claim 1, wherein each $R_1$ and $R_2$ is selected from hydrogen, phenyl, aryl, $C_1$-$C_6$ alkyl, haloalkyl, hydroxyalkyl, aminoalkyl, carboxyalkyl, nitroalkyl, cyanoalkyl, acetamidoalkyl, and acyloxyalkyl; and $R_4$ is alkyl, acyl, aryl, alkoxycarbonyl, or sulfonyl.

6. The compound of claim 1, wherein structure (I) is:

7. The compound of claim 1, wherein the sulfur-ruthenium bond is cleaved upon irradiation with light having a wavelength between about 400 nm to about 800 nm.

* * * * *